US00PP29478P2

(12) United States Plant Patent
Hansen

(10) Patent No.: US PP29,478 P2
(45) Date of Patent: Jul. 10, 2018

(54) *LAGERSTROEMIA* PLANT NAMED 'SPICED PLUM'

(50) Latin Name: ***Lagerstroemia* (L.) hybrid**
Varietal Denomination: Spiced Plum

(71) Applicant: Hans A. Hansen, Zeeland, MI (US)

(72) Inventor: Hans A. Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 15/530,535

(22) Filed: Jan. 25, 2017

(51) Int. Cl.
*A01H 5/00* (2018.01)

(52) U.S. Cl.
USPC ..... Plt./252

(58) Field of Classification Search
USPC ..... Plt./226, 252
See application file for complete search history.

(56) References Cited

PUBLICATIONS

Walters Garden's 2016-2017 Catalogue. https://www.provenwinners.com/sites/provenwinners.com/files/catalogs_pdfs/1-26_front_pages.pdf. 5 pages.*

* cited by examiner

*Primary Examiner* — Susan McCormick Ewoldt
*Assistant Examiner* — Karen M Redden

(57) ABSTRACT

The new and distinct crape myrtle plant named *Lagerstroemia* 'Spiced Plum' has a dense, compact, upright to slightly outright habit forming a rounded mound, is ground hardy to at least USDA zone 6 and shows resistance to leaf spot and powdery mildew. The lightly fragrant flowers are raspberry-purple opening from rosy-red buds on dark red stems, and foliage emerges tinted with burgundy red and slowly matures to deep green. The new plant is useful for landscaping as a specimen or en masse, or for use in showy containers.

1 Drawing Sheet

Botanical genus and species: *Lagerstroemia* (L.) hybrid. Variety denomination: 'Spiced Plum'.

BACKGROUND OF THE INVENTION

The present invention relates to a new and distinct cultivar of *Lagerstroemia* plant, commonly known as crape myrtle, and hereinafter referred to by the cultivar name 'Spiced Plum' or the "new plant." 'Spiced Plum' is grown primarily as an ornamental for landscape use and for use as a potted plant and is the result of an ongoing breeding program to produce new and improved garden worthy plants for the ornamental market. The new plant was the result of seed collected by the inventor in fall of 2012 at a wholesale perennial nursery in Zeeland, Mich., USA using the unreleased proprietary hybrid known as H10-11-28 (not patented) as the seed or female parent, the specific male or pollen parent is an unidentified sibling of H10-11-28 from the isolation block area.

No plants of *Lagerstroemia* 'Spiced Plum' have been sold, in this country or anywhere in the world, by this or any name, prior to the filing of this application, nor has any disclosure of the new plant been made prior to the filing of this application with the exception of that which may have been disclosed or sold within one year of the filing of this application and was either derived directly or indirectly from the inventor.

*Lagerstroemia* 'Spiced Plum' was initially asexually propagated by stem cuttings at a wholesale perennial nursery in Zeeland, Mich., USA in 2014. The resultant plants from successive generations have demonstrated that the new plant has remained stable and true to type in multiple generations of asexual propagation.

SUMMARY OF THE INVENTION

Plants of the new cultivar 'Spiced Plum' have not been observed under all possible environmental conditions. The phenotype may vary somewhat with changes in light, temperature, soil and available moisture and fertility without, however, any variance in genotype.

The following traits have been repeatedly observed and are determined to be unique characteristics of 'Spiced Plum'. Among the characteristics in combination which distinguish 'Spiced Plum' as a new and distinct cultivar, unique from all other cultivars known to the inventor are:

1. Dense, compact, upright to slightly outright growth habit forming rounded mound;
2. Semi-glossy foliage emerges with tinting of burgundy red and matures to deep green;
3. Dark red stems;
4. Bright raspberry-purple flowers open from shiny rosy-red buds;
5. Resistance to *Cercospora* leaf spot and Erisphe powdery mildew;
6. Ground hardy to at least USDA hardiness zone 6.

'Spiced Plum' is distinguished from its female parent, H10-11-28, with flowers that are more raspberry purple. The most similar cultivars known to the inventor include: 'PIILAG-III' U.S. Plant Pat. No. 23,178, 'Trured' U.S. Plant Pat. No. 18,646, 'Whitt VII' U.S. Plant Pat. No. 14,975, 'Cherry Mocha' U.S. Plant Pat. No. 28,281 and co-pending U.S. Plant patent application Ser. No. 15/530,531, 'Bubble Tea'. Compared with 'PIILAG-III' the new plant is shorter and narrower in habit and the flower color has more in the red-purple hue. 'Whitt VII' is much taller and wider and the flower color is deeper oxblood red. Compared with 'Cherry Mocha' the new plant has less burgundy tinting in the foliage and the flowers are a lighter color of raspberry purple rather than the bright cherry red.

BRIEF DESCRIPTION OF THE DRAWINGS

The accompanying color photographs illustrate the flower and foliage characteristics and the overall appearance of 'Spiced Plum', showing the colors as true as it is reasonably possible to obtain in color reproductions of this type. Colors in the photographs may differ slightly from the color values cited in the detailed botanical description which accurately describe the colors of the new *Lagerstroemia*.

DETAILED BOTANICAL DESCRIPTION

Figure 1:
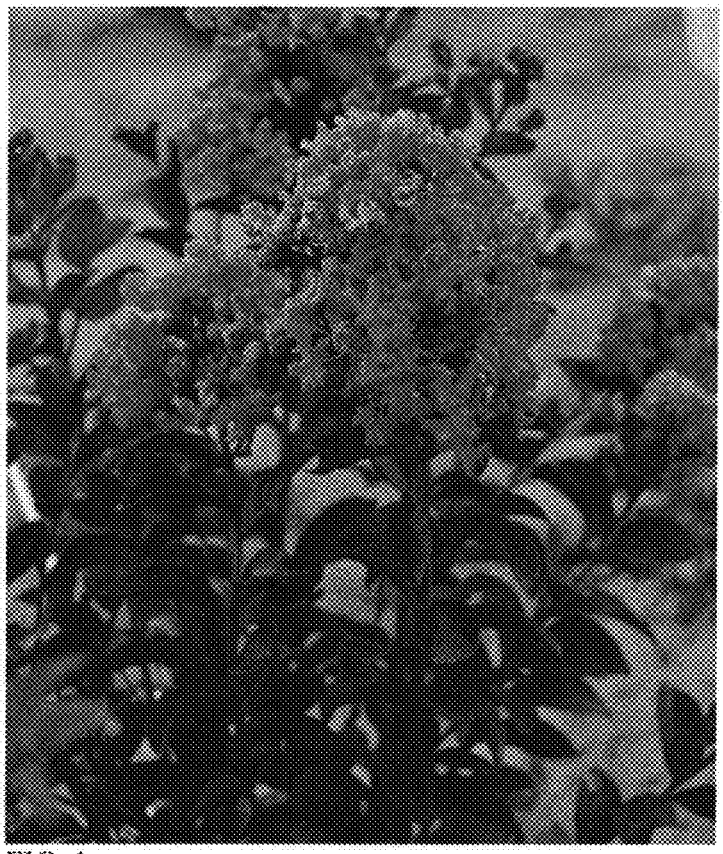
FIG. 1 shows an upright branch with new and mature foliage and flowers.
Figure 2:
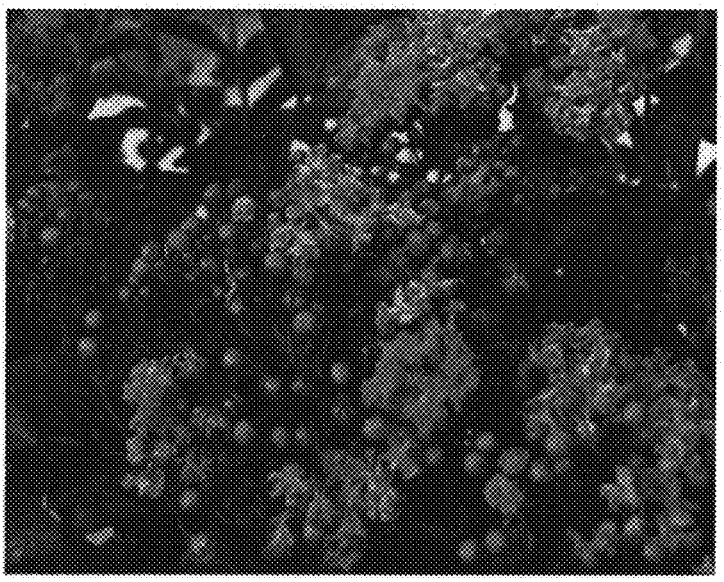
FIG. 2 shows a close-up for the flowers and buds.

The following color references are based on the 2001 edition of The Royal Horticultural Society Colour Chart except where common dictionary terms are used. The following observations and size descriptions are of approximately four-year-old plants grown in a loamy-sand, full-sun, open trial bed in Zeeland, Mich., USA with supplemental water and fertilizer as needed. The phenotype may vary slightly with different environmental conditions, such as temperature, light, fertility, moisture and maturity levels, but without any change in the genotype.

Botanical classification: *Lagerstroemia* L.;

Parentage: Female, or seed parent H10-11-28; the male, or pollen parent is crossed with an unidentified sibling of H10-11-28;

Propagation: Terminal softwood stem cuttings;

Time to initiate roots: About three weeks;

Growth rate: Moderate; about 10 weeks to finish and flower in a 3.7 liter container from a 65 mm liner;

Plant description: Deciduous, woody, narrow, compact flowering shrub; about nine mainly upright to outward primary stems; freely branched;

Root description: Fine, numerous, fibrous, well-branched;

Plant habit: About 52 cm high from the soil level to the top of the inflorescences; about 58 cm wide with no pinching, pruning or plant growth regulators;

Stems: To about 40.0 cm long from soil to base of flowers and about 12.0 mm diameter at base, terete; young stems terete and four longitudinal carinae, along line on either side of petioles;

Stem color: Woody basal 15 cm of between RHS 165D and RHS 166D with exfoliating striations of nearest RHS 200C; young developing stems nearest RHS 183C and striated with between RHS 179C and RHS 179D;

Node: About 18 to 22 per main stem; internode length average about 1.9 cm;

Node color: Same as surrounding stem;

Foliage description: Sub-opposite to alternate; simple; ovate; margin ciliolate; slightly involute; acuminate apex; rounded to cuneate base; to about 4.8 cm long and about 3.2 cm wide; average about 4.4 cm long and 3.0 cm wide; adaxial and abaxial glabrous and lustrous;

Abaxial leaf color: Young emerging leaf nearest RHS 187A with undertone of nearest RHS 146A; mature leaf nearest RHS 146B;

Adaxial leaf color: Young emerging foliage nearest RHS 148A with tinting of nearest RHS 187A; mature leaf nearest RHS 137A;

Adaxial and abaxial ciliate margin color: Nearest RHS 187B throughout season;

Veins: Pinnate, puberulent adaxial and abaxial;

Vein color: Young emerging leaf adaxial midrib and lateral veins nearest RHS 187B; young emerging leaf abaxial midrib and lateral veins nearest RHS 185A; mature adaxial midribs and lateral veins nearest RHS 146C; mature abaxial midribs nearest RHS 145D and lateral veins nearest RHS 145C;

Petiole: Very short to sessile, slightly puberulent abaxial; slightly applanate adaxial; to about 1.0 mm long and 2.0 mm across;

Petiole color: Young adaxial and abaxial nearest RHS 185A, mature adaxial and abaxial nearest RHS 145C;

Inflorescence: Panicle; terminal panicles up to about 80 flowers; average about 50 flowers; up to about 28.0 cm long and about 22.0 cm across; beginning late-summer and continuing until fall, for about six weeks;

Buds: Globose with slightly cuspidate apex and rounded base; laevigate; glabrous; about 9.0 mm tall and about 8.0 mm diameter one day prior to opening;

Bud color: Between RHS 179A and RHS 180A;

Flowers: Perfect; regular; actinomorphic; terminal panicle; individually about 2.5 cm across and about 20.0 mm tall; lasting about two days;

Flower fragrance: Sweet, light;

Peduncle: Terete with four longitudinal carinae; about 3.0 mm diameter at base, about 28.5 cm long;

Peduncle color: Lower portion nearest RHS 183C and striated with between RHS 179C and RHS 179D and distal portion blend between RHS 183C and RHS 187C;

Pedicel: Terete, about 5.0 mm long and 1.0 mm diameter;

Pedicel color: Blend between RHS 183C and RHS 187C;

Sepals: Fused in about the basal 5.5 mm; acute apex, entire margin; glabrous and laevigate both adaxial and abaxial; persistent; about 9.0 mm long and individually about 3.5 mm long above the fusion and about 3.0 mm wide at fusion point; zonate with bands of different colors in the apex, below the apex and below the fused portion;

Sepal color: Adaxial basal 5.5 mm nearest RHS 150D, portion below apex nearest RHS 184B and apex between RHS 194C and RHS 194D; abaxial basal 5.5 mm nearest RHS 145B, portion below apex nearest RHS 183B and apex nearest RHS 181B;

Petals: Six; stalked; glabrous; blade intensely ruffled or crisped; margin crisped; blade with rounded apex and cordate to sagittate base, to about 12.0 mm across and 13.0 mm long; claw base adnate to calyx, to about 6.0 mm long and 0.5 mm diameter; overall about 1.8 cm long; blade to about 9.0 mm long and 12.0 mm across;

Petal color: Blade adaxial and abaxial between RHS 72A and RHS 72B; claw nearest RHS 63B;

Androecium:

*Stamens*.—Total about 36; typically six longer and about 30 shorter.

*Filaments*.—Longer stamens to about 15.0 mm long and about 0.5 mm diameter, curled about 180 degrees in distal 5.0 mm; shorter filaments about 10.0 mm long and curled about 360 degrees in the distal 5.0 mm, and less than 0.3 mm diameter; color of longer filaments base nearest RHS 61B and apical 5.0 mm nearest RHS 155A; color of short filaments nearest RHS 62D.

*Anthers*.—Flattened ellipsoid; more developed on longer stamens to about 1.2 mm long and 1.0 mm across, on shorter stamens about 1.0 mm long and about 0.7 mm across; color nearest RHS 174C.

*Pollen*.—Abundant on longer stamens; color nearest RHS 9C.

Gynoecium: One;

*Style*.—Terete; helicoid; glabrous; about 4.5 mm natural length; stretched to about 19.0 mm long and 1.0 mm diameter; color between RHS N144D and RHS 146D.

*Stigma*.—Globose; about 0.7 mm diameter; color nearest RHS 200C.

*Ovary*.—Superior; globose; laevigate; about 2.0 mm tall and 2.0 mm diameter; color nearest RHS 11B.

Fruit: Globose; glabrous; typically five-valved dehiscent capsule; about 7.0 mm diameter; apex rostrate; base rounded;

Fruit color: Nearest RHS 200A;

Seed: Lunate to lanceolate samara; about 6.0 mm long and 2.2 mm across at widest point and 1.0 mm thick at embryo;

Seed color: Nearest RHS 199D at thin portion and embryo portion nearest RHS N199B;

Disease resistance: *Lagerstroemia* 'Spiced Plum'; has shown resistance to powdery mildew and black leaf spot, *Erisphe* and *Cercospora* fungi, respectively. Other resistance beyond that typical for crape myrtle has not been observed. The new plant's root system is capable of withstanding cold temperatures typical of those found in USDA zone 6.

It is claimed:

1. A new and distinct cultivar of crape myrtle plant named *Lagerstroemia* 'Spiced Plum' essentially as herein illustrated and described.

* * * * *